US005672502A

United States Patent [19]
Birch et al.

[11] Patent Number: 5,672,502
[45] Date of Patent: Sep. 30, 1997

[54] ANIMAL CELL CULTURE

[75] Inventors: John Robert Birch, High Wycombe; Robert Charles Boraston, Reading, both of United Kingdom

[73] Assignee: Celltech Therapeutics Limited, Berkshire, United Kingdom

[21] Appl. No.: 397,682

[22] Filed: Feb. 28, 1995

Related U.S. Application Data

[63] Continuation-in-part of Ser. No. 90,551, Jul. 9, 1993, abandoned, which is a continuation of Ser. No. 51,745, Apr. 7, 1987, abandoned.

[30] Foreign Application Priority Data

Jun. 28, 1985 [GB] United Kingdom .................. 8516415

[51] Int. Cl.$^6$ .............................. C12N 5/02; C12N 5/06; C12N 5/10; C12N 5/20
[52] U.S. Cl. .............................. 435/240.25; 435/240.26; 435/240.27; 435/240.3; 435/240.31
[58] Field of Search .................... 435/240.25, 240.26, 435/240.27, 240.3, 240.31

[56] References Cited

U.S. PATENT DOCUMENTS

| | | |
|---|---|---|
| 3,926,723 | 12/1975 | Green et al. . |
| 3,951,740 | 4/1976 | Gresser et al. . |
| 4,537,860 | 8/1985 | Tolbert . |

FOREIGN PATENT DOCUMENTS

| | | |
|---|---|---|
| 117059 | 8/1984 | European Pat. Off. . |
| 0125023 | 11/1984 | European Pat. Off. . |

OTHER PUBLICATIONS

American Society for Microbiology, Mar. 1985, p. 241, "Abstracts of the Annual Meeting of the American Society for Microbiology", S. Reuveny et al.
Develop. Biol. Standard (1995) pp. 185–197, "Production of Monoclonal Antibodies in Culture", S. Reuveny et al.
Biochemical Society Transactions, (1985), vol. 13, pp. 10–12, "Production of Monoclonal Antibodies in Large-scale Cell Culture", John R. Birch et al.
Chemtech, Jun. 1987, pp. 378–381, "Cells Sell—Large-scale production of Monoclonal Antibodies", John R. Birch.
Glutamine Metabolism in Mammalian Tissues, (1984) pp. 247–254, "Glutamine Metabolism by Cultured Mammalian Cells", H. R. Zielke et al.
Biotechnology Letters, vol. 5, No. 9, (1983) pp. 573–578, "In Vitro Production of High Titre Monoclonal Antibody By Hybridoma Cells in Dialysis Culture", S. R. Adamson et al.
Antimicrobial Agents and Chemotherapy, Mar. 1979, vol. 15, No. 3, pp. 420–427, "Large–Scale Production and Concentration of Human Lymphoid Interferon", Frederick Klein et al.
In Vitro, (1970), vol. 6, No. 2, pp. 89–108, "A Survey of Commercially Available Tissue Culture Media", Helen J. Morton.
Proc. Roy. Soc. B. vol. 168, (1967) pp. 421–438, "The Uptake of Amino Acids By Mouse Cells (strain LS) During Growth in Batch Culture and Chemostat Culture: The Influence of Cell Growth Rate", J. B. Griffiths et al.
Science, vol. 130, (1959), pp. 432–437, "Amino Acid Metabolism in Mammalian Cell Cultures", Harry Eagle.
Federation Proceedings, vol. 17, (1958), p. 508, "Nutritional Requirements for Poliovirus Synthesis in HeLa Cells", J. E. Darnell et al.
Virology, vol. 6, (1958), pp. 556–566, "Glucose and Glutamine in Poliovirus Production by HeLa Cells", James E. Darnell, Jr. et al.
Science, vol. 122, No. 3168, Sep. 16, 1955, pp. 501–504, "Nutrition Needs of Mammalian Cells in Tissue Culture", Harry Eagle.
Biological Institute of the Carlsberg Foundation, pp. 218–230, "Protein Metabolism of Tissue Cells in Vitro. 7. The Chemical Nature of Some Obligate Factors of Tissue Cell Nutrition", G. Ehrensvard et al.
Animal Cell Biotechnology, vol. 1, (1985), pp. 195–210, "The Cultivation of Animal Cells in Continuous–Flow Culture", Michael G. Tovey.
Advances in Biotechnological Processes, vol. 2, (1983), pp. 97–110, "Large–scale Production of Extrinsic (Tissue–Type) Plasminogen Activator From Human Melanoma Cells", C. Kluft et al.
Annals N.Y. Academy of Science, vol. 413, (1983), pp. 355–372, "Large–scale Production of Mammalian Cells and Their Products: Engineering Principles and Barriers to Scale–up", M. W. Glacken et al.
Third European Congress on Biotechnology, vol. 1, (1984), pp. 173–179, "Repeated Fed–Batch Cultivation of Human Lymphocytic Cells", J. Ingham et al.
Chem. Abs., vol. 101, (1984), p. 499, "Operation Charts for a Successive Fed–Batch Fermentation of Alcohol", Nagamune et al.
Chem. Abs., vol. 99, (1983), p. 459 "Comparison of Cell Productivities Among Fed–Batch, Repeated Fed–Batch and Continuous Cultures at High Cell Concentration" Mori et al.
In Vitro, vol. 7, No. 5, pp. 330–343, (1972), "Amino Acid Utilization by L–M Strain Mouse Cells in a Chemically Defined Medium", Gary D. Stoner et al.

(List continued on next page.)

*Primary Examiner*—Lila Feisee
*Assistant Examiner*—Nancy A. Johnson
*Attorney, Agent, or Firm*—Spencer & Frank

[57] ABSTRACT

Process for the fed-batch culture of animal cells comprises culturing the cells in nutrient medium characterized in that during the culture the medium is supplemented with a combined feed of one or more energy sources and one or more amino acids, and culturing is continued into the decline phase of the culture to provide the product(s) of the cells. The process is particularly applicable to genetically modified cells, especially hybridoma cell cultures to produce monoclonal antibodies. Preferably, the supplemental feed is fed to the culture at a slow rate over a prolonged period. Very significant enhancement of overall product yield may be obtained.

18 Claims, 7 Drawing Sheets

OTHER PUBLICATIONS

Annals N.Y. Academy of Science, vol. 369, (1981) pp. 33–46, "Optimizing Culture Conditions for the Production of Animal Cells in Microcarrier Culture", J. M. Clark, et al.

Journal of Immunological Methods, vol. 86, (1986), pp. 53–59, "Factors Affecting Cell Growth and Monoclonal Antibody Production in Stirred Reactors", S. Reuveny et al.

Biotechnology and Bioengineering, vol. XXIII, (1981), pp. 249–253, "Maximum Cell Productivity by Repeated Fed–Batch Culture for Constant Yield Case", W.A. Weigand.

"Introduction to Research with Continuous Cultures", pp. 4–9, H. E. Kubitschek, Prentice–Hall, Inc., Englewood Cliffs, N.J.

Macmillan Dictionary of Genetics & Cell Biology, (1987), pp. 70, 294 and 376, Norman Maclean, The Macmillan Press, Ltd.

Biotechnology and Bioengineering, vol. X, (1968) pp. 373–383, "Continuous Flow Cultures of a HeLa Cell Line as a Basis for a Steady Supply of Rubella Virus", Björn Holmström.

Biotechnology and Bioengineering, vol. XV, (1973), pp. 257–269, "Fed–Batch Hydrocarbon Fermentation With Colloidal Emulsion Feed", Fumitake Yoshida et al.

Biotechnology, vol. 1, (1981), pp. 458, 462, 472, "Batch and Continuous Culture of Microbial, Plant and Animal Cells", H. J. Rehm et al., ed.

Macmillan Dictionary of Biotechnology, (1986), pp. 34, 35, 54, 55, 70, 71, plus two additional pages, J. Coombs, The Macmillan Press, Ltd.

Dictionary of Microbiology, (1981), Paul Singleton and Diana Sainsbury, ed., John Wiley & Sons. Ltd. (Ten pages).

Culture of Animal Cells—A Manual of Basic Technique, 2nd Ed. (1987), pp. 311, 7, 8, 127, 132, 134, R. Ian Freshney.

Development Biol. Standard, (1987), vol. 66, pp. 169–175, "Factors Affecting Monoclonal Antibody Production in Culture", S. Reuveny et al.

Monsanto Company, "Perfusion Culture Systems For Production of Mammalian Cell Biomolecules", William R.. Tolbert et al.

Develop. Biol. Standard, vol. 60, (1985), pp. 229–236, "Large Scale Animal Cell Cultivation for Production of Cellular Biologicals," A. L. van Wezel et al.

Develop. Biol. Standard, vol. 60, (1985), pp. 73–79, "Growth Kinetics of Hybridoma Cells: (2) The Effects of Varying Energy Source Concentrations", K. Low et al.

Biotechnology and Bioengineering, vol. 28, (1986) pp. 1376–1389, "Reduction of Waste Product Excretion via Nutrient Control: Possible Strategies for Maximizing Product and Cell Yields on Serum in Culture of Mammalian Cells", M.W. Glacken et al.

The Journal of Biological Chemistry, vol. 254, No. 8, (1979), "Evidence That Glutamine, Not Sugar, Is The Major Energy Source For Cultured HeLa Cells", Lawrence J. Reitzer, et al., pp. 2669–2676.

Culture of Animal Cells—A Manual of Basic Technique, (1983), pp. 71, 74, 119–128, R. Ian Freshney, Alan R. Liss, Inc., New York.

Yamane and Shimizu, Advance in Biochem. Eng/Biotech 30:147–194 1984.

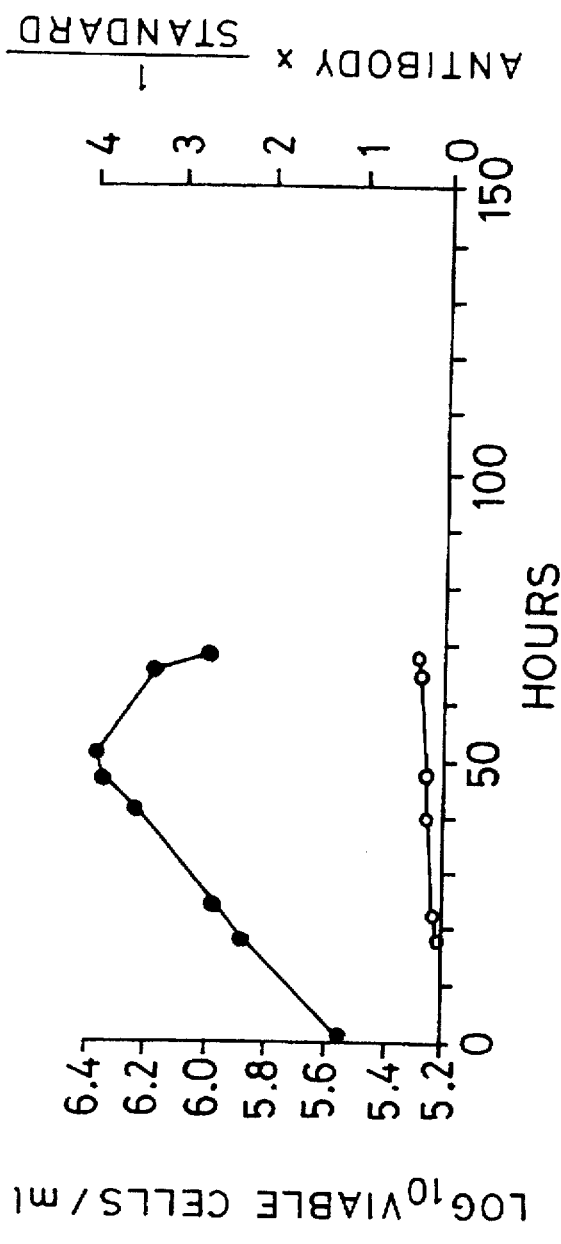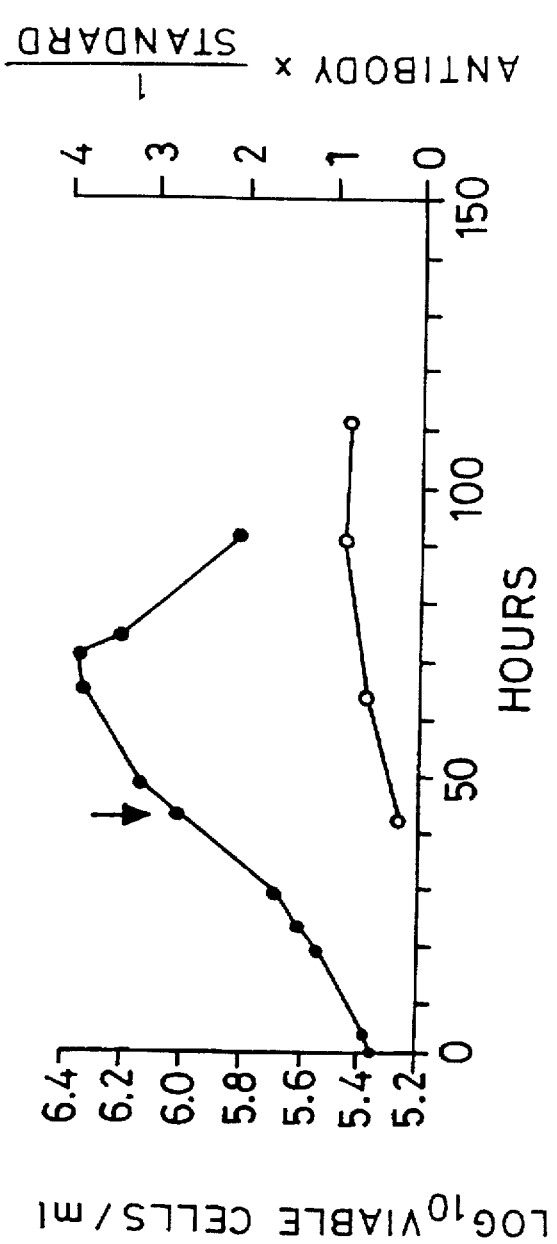
FIG. 1(a)
DMEM + 3% FCS
No additions
FIG. 1(b)
DMEM + 3% FCS
1 × 4mM glutamine

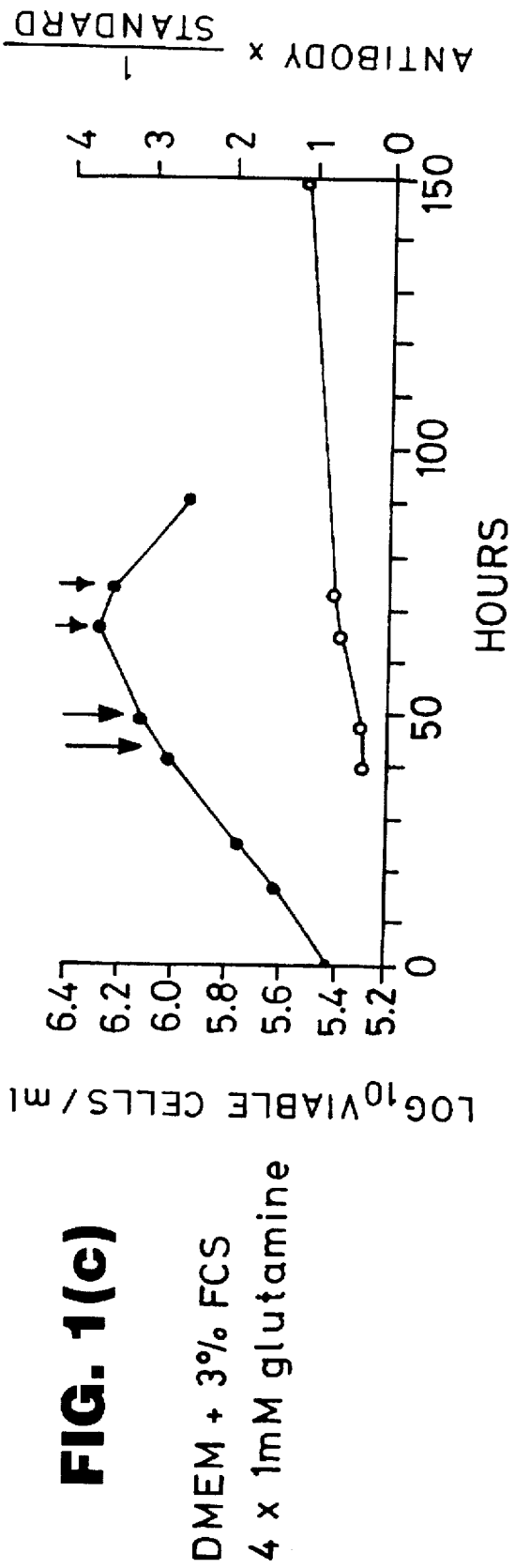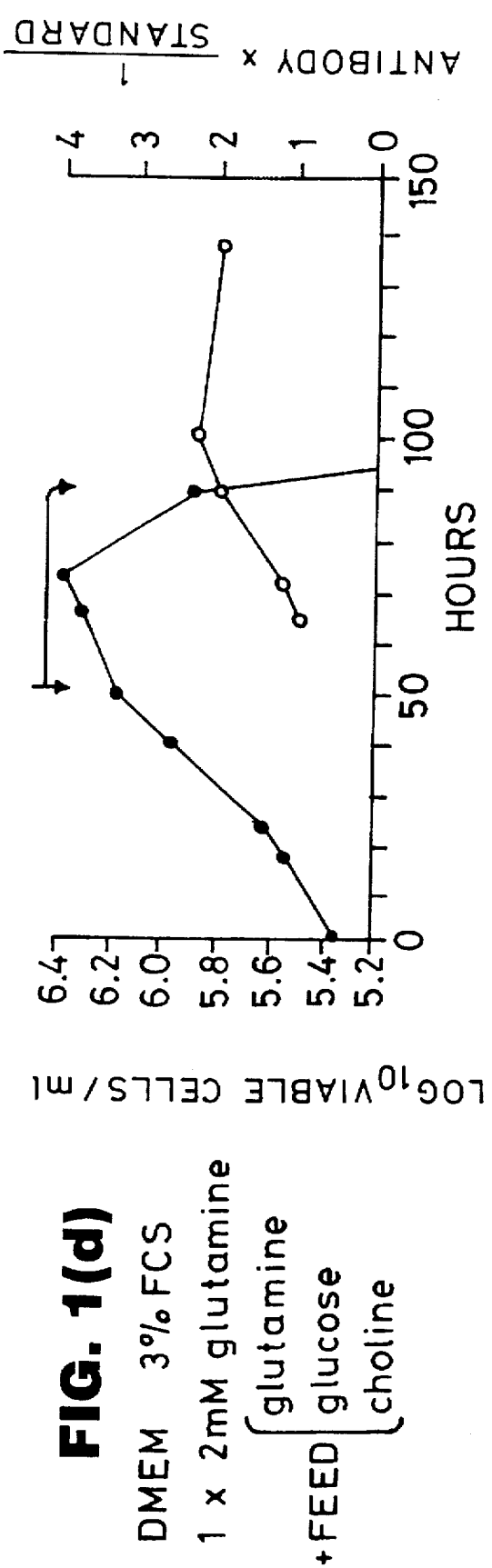
FIG. 1(c)
DMEM + 3% FCS
4 × 1mM glutamine
FIG. 1(d)
DMEM 3% FCS
1 × 2mM glutamine
+ FEED { glutamine, glucose, choline }

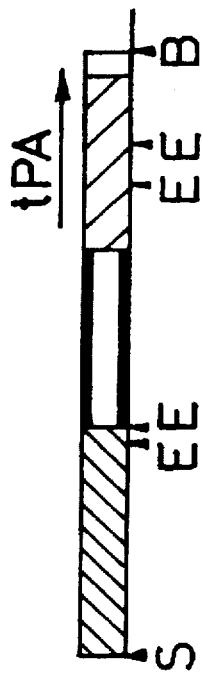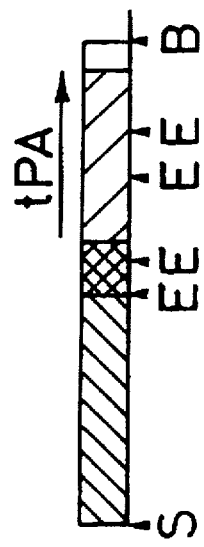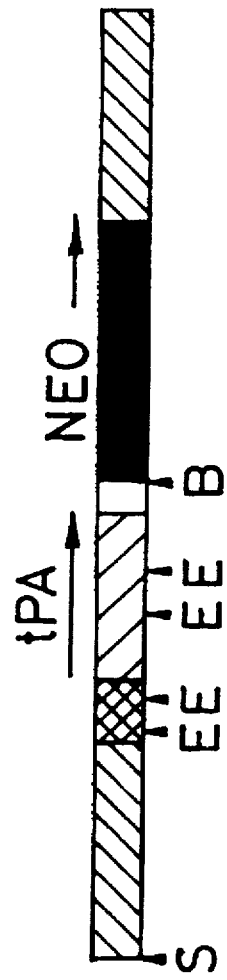

ANIMAL CELL CULTURE

CROSS-REFERENCE TO RELATED APPLICATION

This application is a continuation-in-part of U.S. patent application Ser. No. 08/090,551, filed Jul. 9, 1993, now abandoned, which is a continuation of applicants' U.S. patent application Ser. No. 07/051,745 filed Apr. 7, 1987, now abandoned, each of which are incorporated herein by reference. This application claims foreign priority to patent application PCT/GB86/00383, filed Jun. 30, 1986 and Great Britain patent application 8516415 filed Jun. 28, 1985, each of which is incorporated herein by reference.

FIELD OF THE INVENTION

This invention relates to animal cell culture and in particular to processes for the culture of the animal cells to produce polypeptide and protein products.

BACKGROUND TO THE INVENTION

In recent years, there has been considerable and ever increasing interest in the culturing of animal cells to provide useful products. This interest has been heightened by recent advances in molecular biology which have made it possible to prepare genetically modified animal cells which may be cultured to produce desired polypeptide and protein products. Thus cell fusion techniques based on the work of Kohler & Milstein (Nature 256, 495–597) allow preparation of hybrid cell lines, i.e. hybridomas, which may be cultured to produce monoclonal antibodies. Also recombinant DNA techniques have been applied to animal cells to provide cell lines, transformed with heterologous genes, which may be cultured to produce corresponding gene products. In many cases it has been found that animal host cells are more desirable than microbial host cells, e.g. bacteria and yeast, for production of recombinant products, in particular when the products are complex proteins requiring glycosylation and other post translational modification for full activity. Animal host cells provide environments akin to the natural cellular environments in which the products are produced.

In order to apply animal cell culture to the industrial production of desired products it is necessary to develop culture processes which produce the products in sufficient quantity and at a commercially viable cost. Hitherto, however, most industrial culture processes have been based upon the fermentation of microbial cultures, and comparatively little is known about the factors which affect product yield in cultures of animal cells. It is known (see published International Patent Application WO 84/00777-Unisearch), for example, in microbial batch culture production of secondary metabolites, such as antibiotics, to continuously add to the culture medium those nutrients found to be essential for production of the secondary metabolite; though apparently only a limited improvement in the long term rate of secondary metabolite was obtained.

Five basic methods exist for culturing animal cells. Although there are variations within each process, these are not relevant to the general way in which the process is operated. The five processes are described below.

Batch Culture

Batch culture is the earliest form of culture. It is carried out by placing the cells to be cultured into a fixed volume of culture medium and allowing the cells to grow. Cell numbers increase, usually exponentially, until a maximum is reached, after which growth becomes arrested and the cells die. This may be due either to exhaustion of a nutrient or accumulation of an inhibitor of growth. To recover product, cells are removed from the medium either when the cells have died or at an earlier, predetermined point.

Thus, batch culture is characterised in that it proceeds in a fixed volume (since nothing is added after placing the cells in the medium), for a fixed duration (dependent on the length of time the cells survive) with a single harvest and with the cells dying or being discarded at the end of the process.

Fed Batch Culture

This is a variation on ordinary batch culture and involves the addition of a feed to the batch. Cells are cultured in a medium in a fixed volume. Before the maximum cell concentration is reached, specific supplementary nutrients are added to the culture. The volume of the feed is minimal compared to the volume of the culture. This is the type of process over which the present invention is a considerable improvement.

Fed batch culture is also characterised in that it proceeds in a substantially fixed volume, for a fixed duration, and with a single harvest either when the cells have died or at an earlier, predetermined point.

Serial Subculture (Repeated Batch Culture)

In serial subculture, the cells are placed in a culture medium and grown to a desired cell density. To avoid the onset of a decline phase and cell death, the culture is diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state.

Serial subculture is characterised in that the volume of culture is always increasing stepwise, there can be multiple harvests, the cells continue to grow and the process can continue for as long as desired.

Continuous Chemostat or Turbidostat Culture

In chemostats and turbidostats, the cells are initially grown in a fixed volume of medium. To avoid the onset of the decline phase, a pumped feed of fresh medium is initiated before maximum cell concentration is reached. Culture, containing a proportion of the cells, is continuously removed from the vessel to maintain a constant volume. The process removes a product, which can be continuously harvested, and provides a continuous supply of nutrients, which allows the cells to be maintained in an exponentially growing state. The process can, in theory, be operated indefinitely.

Continuous culture is characterised by a continuous increase in culture volume, of product and maintenance of exponentially growing culture. There is no death or decline phase.

Perfusion Culture

This is similar to continuous culture except that, when the medium is pumped out of the reactor, cells are not removed.

As with continuous culture, perfusion culture is an increasing volume system with continuous harvest which can, in theory, continue indefinitely.

Hybridoma cells have been cultured in Dulbecco's Modified Eagle's Medium (DMEM) to produce monoclonal antibodies (Sacks & Lennox, Vox Sang. 40:99–104 (1981)). More recently, a method of promoting protein or antibody production from a protein or antibody-producing cell of mammalian origin has been described (GB 2153830A - Damon Biotech) comprising the step of culturing the cell in a hypertonic medium having an osmolarity no less than about 340 milliosmoles. GB 2153830A describes, in particular, the culture of encapsulated hybridoma cells and the addition of an excess of amino acids to make the culture medium hypertonic. However, our studies of animal cell culture, in particular hybridoma cell culture indicate that other factors besides osmolarity are important in determining levels of protein produced from culturing animal cells.

We have studied the kinetics of cell growth and antibody production in simple batch cultures of hybridoma cells in a culture medium comprising Dulbecco's Modified Eagle's Medium (DMEM), supplemented with foetal calf serum (FCS). Following an exponential growth phase, glutamine in the DMEM becomes depleted at a cell population density of about $2 \times 10^6$ cells/ml, cell growth ceases, the population of viable cells in the culture declines rapidly, and the synthesis of antibody is terminated.

It appeared that the decline in viable cells was due to a lack of essential nutrients in the medium and, in particular, to a lack of glutamine. It is known that glutamine is unstable in culture medium and that some of its degradation products are cytotoxic (especially ammonia and pyrrolidine carboxylic acid). We therefore investigated a simple form of fed batch culture in which glutamine was added during and following the later exponential phase of the culture. A single shot addition of glutamine, added to the culture in the late exponential phase did not substantially affect the maximum cell population density but the culture remained viable for a prolonged period with a resulting increase in total antibody titre.

We also investigated the addition of repeated doses of glutamine in place of the single shot addition. Repeated doses of glutamine (to the same overall added concentration as the previous single shot addition) over a period of 40 hours produced no improvement in cell or antibody yield compared to cultures receiving the single addition.

These results were unexpected. Although exhausted from the medium, glutamine appears not to be the only factor limiting maximum population density since addition of glutamine to the culture does not lead to an increase in maximum viable cell density. Rather, glutamine addition appears to prolong viability of the culture resulting in a small increase in total antibody yield.

We have further studied factors which affect the level of protein production from animal cell cultures. We have unexpectedly discovered that a feed of glutamine and other nutrients, in particular when fed at a low rate and for a prolonged period of time, results in a significant increase in antibody yield of cultured hybridoma cell lines, especially in the decline phase of a batch culture. We have found similar results for the production of heterologous gene products from cultures of transformed animal cells.

SUMMARY OF THE INVENTION

Accordingly the present invention provides a process for the batch culture of animal cells comprising culturing the cells in a nutrient medium, characterised in that during the culture the medium is supplemented with a combined feed of one more energy sources and one or more amino acids, and culturing is continued into the decline phase of the culture to provide the product(s) of the cells.

The present invention arises from the unprecedented discovery that continued feeding of nutrients to an animal cell culture, in particular when fed over a prolonged time period, leads to a significant increase in product yield if the culture is continued into the decline phase. Contrary to expectation continued feeding of nutrients does not increase the maximum viable cell population density but instead appears to prolong the period of viability of the culture beyond the point at which onset of the decline phase would occur in an unfed culture, giving enhanced levels of product formation. In particular, we have found that a combination feed of energy sources and amino acids leads to a very significant increase in overall product yield. Surprisingly this combined feed of energy sources and amino acids does not appear to lead to and increase in maximum viable cell population density.

The reason for this phenomenon is not completely understood. There are two likely explanations for the decline in cell growth which makes the change from the exponential growth phase to the decline phase of the culture. Either one or more nutrients required for cell growth though not required for protein synthesis become depleted and cell growth ceases, or one or more cytotoxic metabolites, such as lactate or ammonia, accumulate in the culture inhibiting further cell growth. Of these two explanations, we favour the latter. Thus, without prejudice, it appears that cell growth is inhibited by cytotoxic metabolite accumulation and continued feeding, as in the process of the invention, serves to prolong viability of the culture giving rise to enhancement of overall product yield; the supplemental nutrients being utilised during the decline phase primarily for protein synthesis and as energy sources rather than for cell growth. It will be appreciated, however, that the above is given as a possible explanation of the phenomenon which we have observed but does not limit the scope of the invention.

The process of the invention may be applied to the culture of animal cells, e.g. mammalian cells, in general, including cells which constitutively produce desired products such as Namalva cells and Bowes melanoma cells. Preferably, however, the process may be applied to the culture of genetically modified cell lines. Thus the cells may be transfected animal cells i.e. animal cells which have been infected with heterologous genes so that the cells may be cultured to produce the corresponding gene products. Such transfected animal cells may include transfected mammalian host cells such as transfected Chinese Hamster Ovary (CHO) cell lines, and in particular include hybridoma and myeloma cell lines which have been transfected with heterologous genes. Most preferably the process may be applied to the culture of cell lines which produce monoclonal antibodies including Epstein Barr Virus (EBV) transformed antibody producing cell lines, and especially hybridoma cell lines prepared by cell fusion techniques.

The process may be applied to any cells which may be batch cultured including anchorage dependant cells, for instance in microcarrier culture, and also encapsulated cells. Preferably, however, the cells are cells which are cultured in suspension.

Any product which may be produced by cultured animal cells may be produced using the process of the invention. Such products typically comprise polypeptide and protein products, and include hormones such as growth hormone, e.g. hGH, lymphokines such as interferon, interleukins, e.g. IL2, recombinant antibody molecules and fragments thereof, industrially and therapeutically useful enzymes such as tPA and enzyme inhibitors such as Tissue Inhibitor of Metalloprotinases (TIMP). Particularly preferred products such are monoclonal antibodies.

The medium may be supplemented with the combined feed at any appropriate time during the culture. The supplemental feed may be commenced after the exponential growth phase of the culture but is preferably commenced during the exponential growth phase especially during the second half thereof. Advantageously, however, the culture is supplemented with the feed over a prolonged period of time. Supplemental feeding may be completed during the exponential growth phase of the culture, but is preferably continued into the stationary growth phase, and may be continued into the decline phase of the culture.

For the purposes of the present description the term "exponential growth phase" means the period of growth up to the point at which maximum viable cell population density is reached.

For example, in a typical suspension culture of hybridoma cells supplemental feeding is commenced from 25 to 150 hours preferably from 40 to 60 hours, and especially at about 50 hours after the start of the culture. For instance, supplemental feeding may be commenced when the cells have grown to a viable cell density of about $1 \times 10^6$ cell ml. Also the feed supplement is provided to the culture for a period of al least 5 to 20, and preferably 10 to 15, hours after the peak of viable cells in the culture has occurred. Moreover, the feed supplement is preferably provided over a total period of from 30 to 100 hours, most preferably from 40 to 60 hours especially about 40 hours. Similar supplemental feeding regimes may be used with hybridoma cells in general, and also transfected hybridoma and myeloma cells. However, it will be appreciated that the time and period of feeding may be varied having regard to the growth characteristics of the cell in question.

Similarly the components of the supplemental feed may be varied in accordance with the particular cell being cultured. Thus the energy source may comprise any suitable energy source for the cell; though it usually comprises at least one carbohydrate energy source, such as a sugar, especially glucose. Other suitable carbohydrate energy sources include disaccharides such as maltose, lactose and sucrose, and monosaccharides such as galactose, fructose, etc. Other possible energy sources comprise; glycerate, glyceraldehyde, etc. Glutamine, in addition to its roles as an amino acid precursor for protein synthesis, is also a major energy substrate for animal cells in culture. Thus the energy source component of the feed may comprise glutamine, usually in combination with a carbohydrate, such as glucose.

The supplemental feed also comprises one or more amino acids typically including glutamine or a precursor thereof e.g. glutamic acid. Usually, however, the supplemental feed comprises a combination of amino acids. The feed may comprise one or a combination of some or all of essential amino acids such as arginine, cystine, glutamine, glycine, histidine, isoleucine, leucine, lysine, methionine, phenylalanine, serine, threonine, tryptophan, tyrosine and valine. The feed may also comprise one or a combination of some or all of non-essential amino acids such as alanine, aspartic acid, asparagine, glutamic acid and proline. (The feed may also contain special amino acids such as hydroxyproline, γ-carboxyglutamate and phosphoserine).

The supplemental feed may comprise other nutrients, such as choline. The feed may also contain growth stimulatory or regulatory factors such as hormones, though these are normally provided in the culture medium at the start of the culture.

It will be appreciated that the amino acid components of the feed are typically L amino acids and may be in the form of salts or precursors thereof. In place of single amino acids, dipeptides and other short peptides may be used to provide the amino acid component of the feed.

The amount of energy source and amino acid components used in the feed may be varied as desired to prolong viability of the culture and provide the substrates required for product synthesis. Preferably, however, the components of the supplemental feed and quantities thereof may be selected by analysis of the culture medium. Thus the feed may comprise those components of the medium which are depleted by growth and the amounts of these components which are fed to the culture are preferably such as to restore and maintain the concentrations of the components at the levels present in the medium at the start of the culture. Typically the feed is such as to maintain those media components which are used either as energy substrates or as biosynthesis precursors in excess for the duration of the culture.

Any suitable culture medium may be used at the start of the culture. A particularly preferred culture medium is Dulbecco's Modified Eagle's Medium (DMEM), usually supplemented with serum e.g. FCS; though modifications of DMEM and other similar culture media may be used as the basis of the culture process. Low-serum media, serum-free media and low-protein media may be used as appropriate.

Thus in a preferred embodiment the invention provides a process for the batch culture of animal cells comprising culturing the cells in nutrient medium, characterised in that, during the culture the medium is supplemented with a combined feed of energy sources, amino acids and other nutrients which have been depleted by growth of the cells, and the culture is continued into the decline phase thereof to provide the products of the cells.

The supplemental feed may be fed to the culture medium in any appropriate fashion. The feed may be supplied as single "shot" addition or preferably as a plurality of "shot" additions over a prolonged period of time. Such shot additions may comprise separate components, i.e. energy sources and amino acids, or any suitable combination of the components. Preferably, however, some or all of the components are added continuously over a prolonged period of time.

The components of the feed may be added to the culture in the form of solids e.g. powdered, or in the form of slurries or preferably as solutions.

In particular, so called "insoluble" amino acids such as cystine, tyrosine and tryptophan which are only sparingly soluble at neutral pH may be added, preferably as a shot addition, in the form of a slurry. Other so-called "soluble" amino acids are preferably added in the form of solutions. Most preferably, however, a solution comprising an energy source, e.g. glucose, and "soluble" amino acids, and optionally also choline, is pump fed to the culture over a prolonged period of time. Such pumped feeds may be added to the medium after "shot" addition of feed components such as glutamine and "insoluble" amino acids.

The exact composition of the supplemental feed, the components and quantities thereof, depends upon the particular type of cell which is being cultured. For example, however, in a typical hybridoma cell culture the main components of the feed are glutamine and carbohydrate energy source, such as glucose. The total glutamine feed is usually in the range from 0.5 to 3, preferably from 0.8 to 1.6, especially from 1 to 1.5 grams per liter of the culture. When the glucose is used as an energy source the total glucose feed is usually from 1–10, preferably from 3 to 6, especially from 4 to 5 grams per liter of the culture. Equivalent amounts of other carbohydrate energy sources may be also used with similar quantities of glutamine.

The amino acid feed for typical hybridoma cultures may comprise in addition to glutamine, some or all of the following amino acids (including salts and precursors): cystine, tyrosine, tryptophan, lysine, histidine, arginine, glycine, valine, methionine, threonine, serine, isoleucine, leucine and phenylalanine. Generally the amino acids are present in the medium at the start of the culture. The total amounts of each of the amino acids (excepting glutamine) in the feed is usually from 0 to 300, more usually from 20 to 200 mg per liter of the culture. Preferably, the feed may comprise relatively higher amounts (e.g. 70–130 mg per liter of culture) of lysine, arginine, valine, isoleucine and leucine; intermediate amounts (e.g. 40–70 mg per liter of culture) of tyrosine, threonine and phenylalanine; and relatively low amounts (10–40 mg per liter of culture) of cystine, tryptophan, histidine, glycine, methionine and serine. Preferably also the feed may comprise a relatively low (e.g. 5–20 mg per liter of culture) of choline e.g. as choline chloride.

Using the process of the present invention, we have found that it is possible to obtain significant enhancement of antibody yield from suspension cultures of hybridoma cells. Typically, we have obtained at least 2.5x, often at least 3–4x and sometimes as much as 7x the overall product yield as compared with unfed batch cultures of hybridoma cells. We have also obtained increases of al least 50% in product yield from cultures of EBV-transformed, antibody-producing human cells as compared with unfed cultures. Moreover, we have obtained similar enhancement of product yield from cultures of transfected animal cells, in particular transfected hybridoma and myeloma cells which produce tPA. In preferred embodiments the process of the invention is characterised by substantial product formation after exponential growth of the culture has ceased. Often more than 50% and sometimes as much as 80% of the total product yield is produced after exponential growth has ceased.

BRIEF DESCRIPTION OF DRAWINGS

The invention is further described by way of illustration only in the following examples. The examples refer to the accompanying diagrams in which:

FIG. 1(a)–FIG. 1(e) shows graphs of viable cell density and antibody titre against time of hybridoma cell cultures:

1a A simple batch culture;

1b & c Simple fed batch cultures;

1d & e Fed batch cultures according to the invention.

Figure 1E:
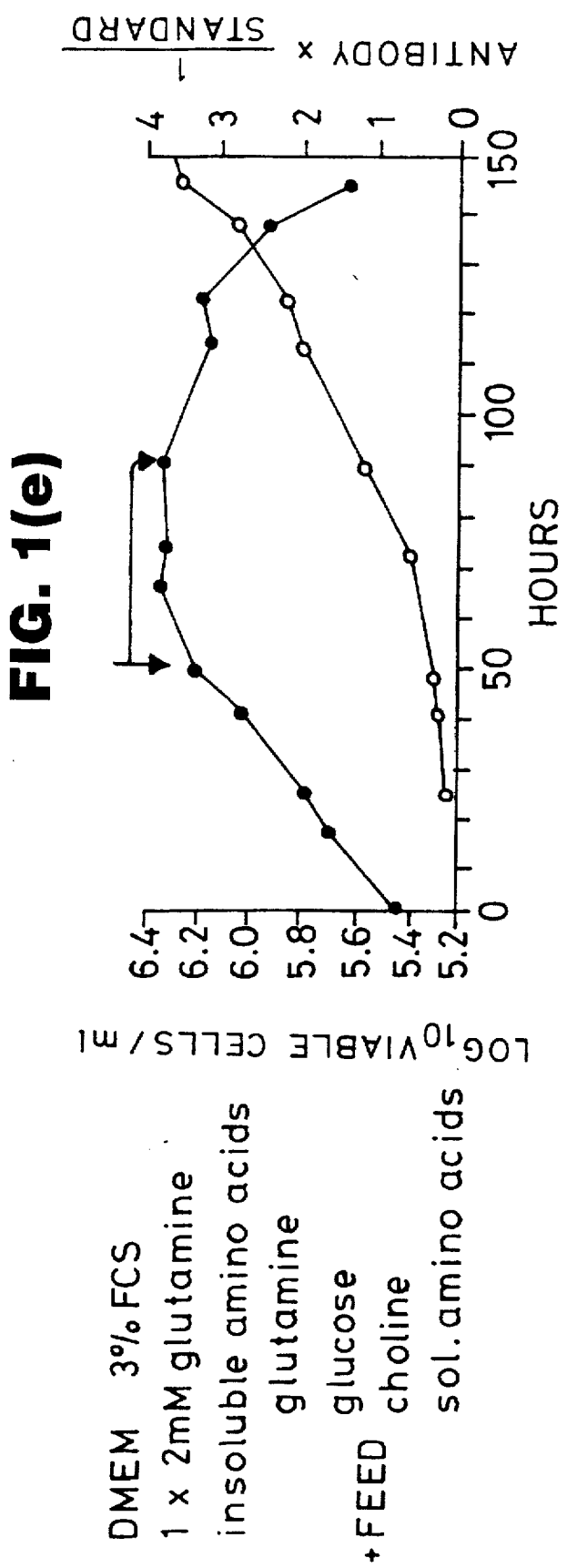
Figure 2:
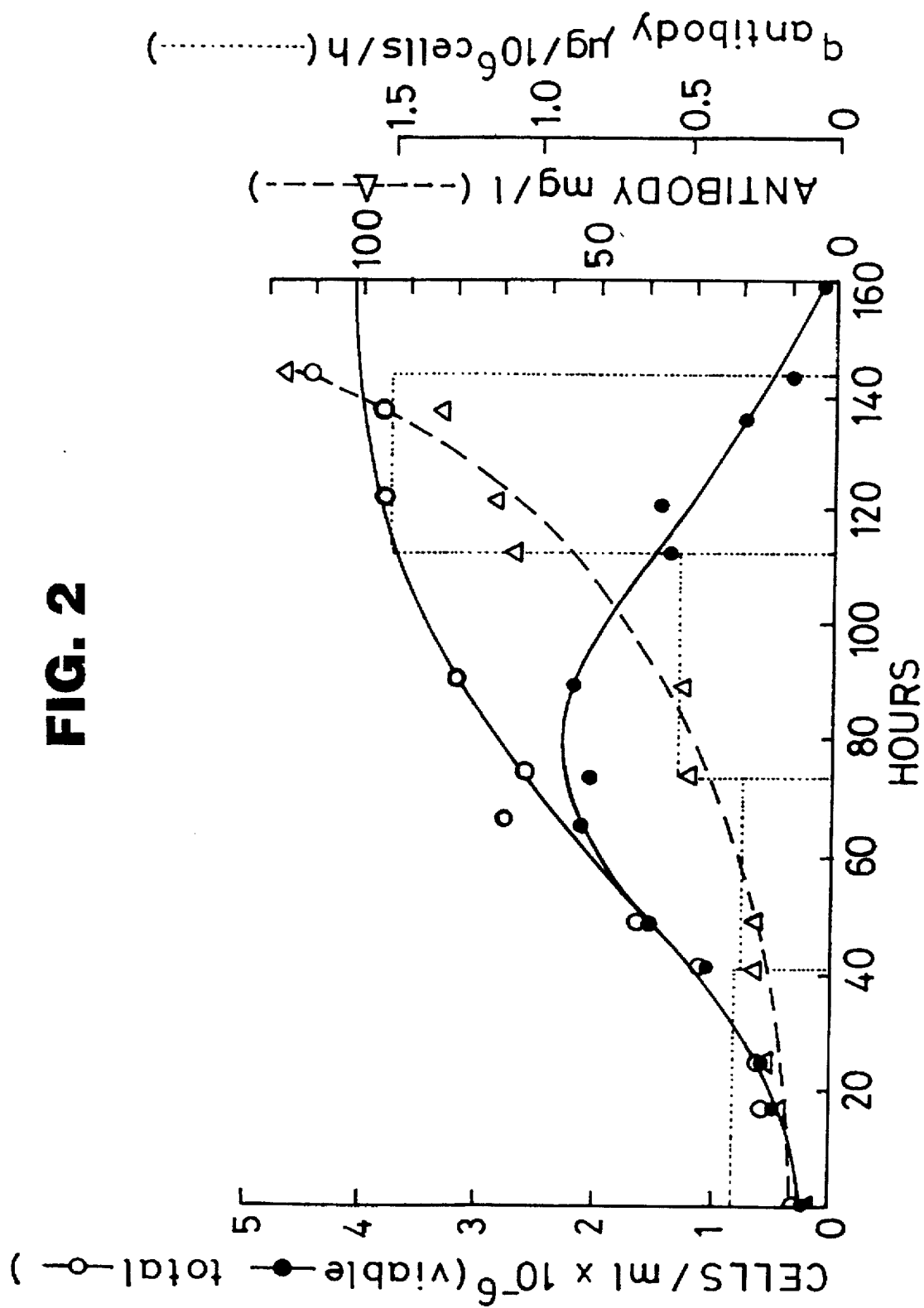

FIG. 2 shows a graph of total cell population density, viable cell density and antibody concentration against time for a culture as in FIG. 1(e).

Figure 3A:
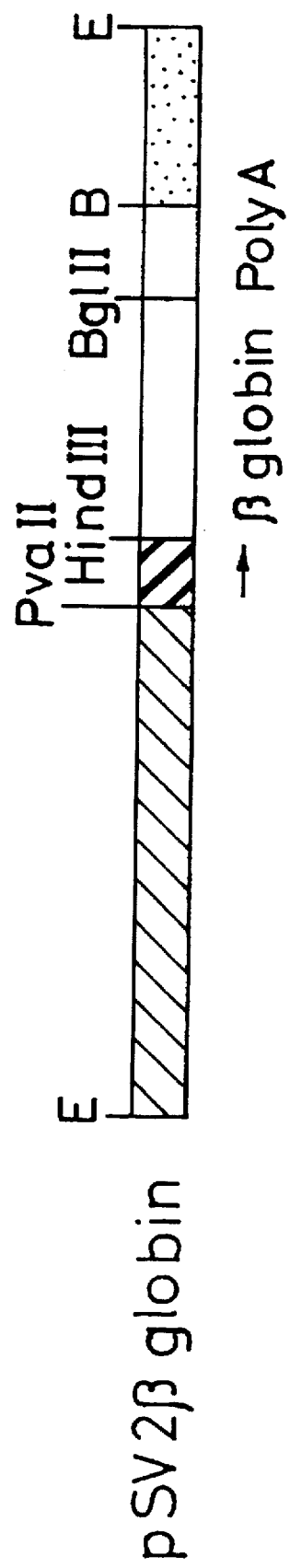
Figure 3B:
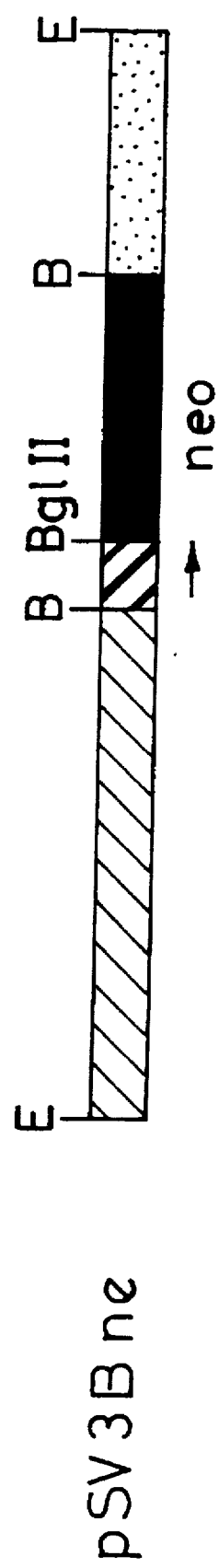

FIG. 3(a)–FIG. 3(e) shows partial restriction maps of plasmids pSV2β globin, (FIG. 3(a)), pSV3Bne (FIG. 3(b)), p3.16 (FIG. 3(c)), pRSV3 (FIG. 3(d)) and pPRI (FIG. 3(e)) (the direction of transcription of the tPA and BPV genes is denoted by arrows). The positions of the restriction enzyme sites for EcoRI, BamHI and SalI are denoted E, B, and S respectively. The origin of the various sequences is denoted:

■ pBR322 derived DNA;

☐ mouse metallothionein promoter;

■ LTR promoter from Rous Sarcoma Virus;

■ tPA cDNA gene;

☐ SV40 polyA site;

■ selection gene;

▨ SV40 early promoter;

▦ SV40 sequences.

Figure 4:
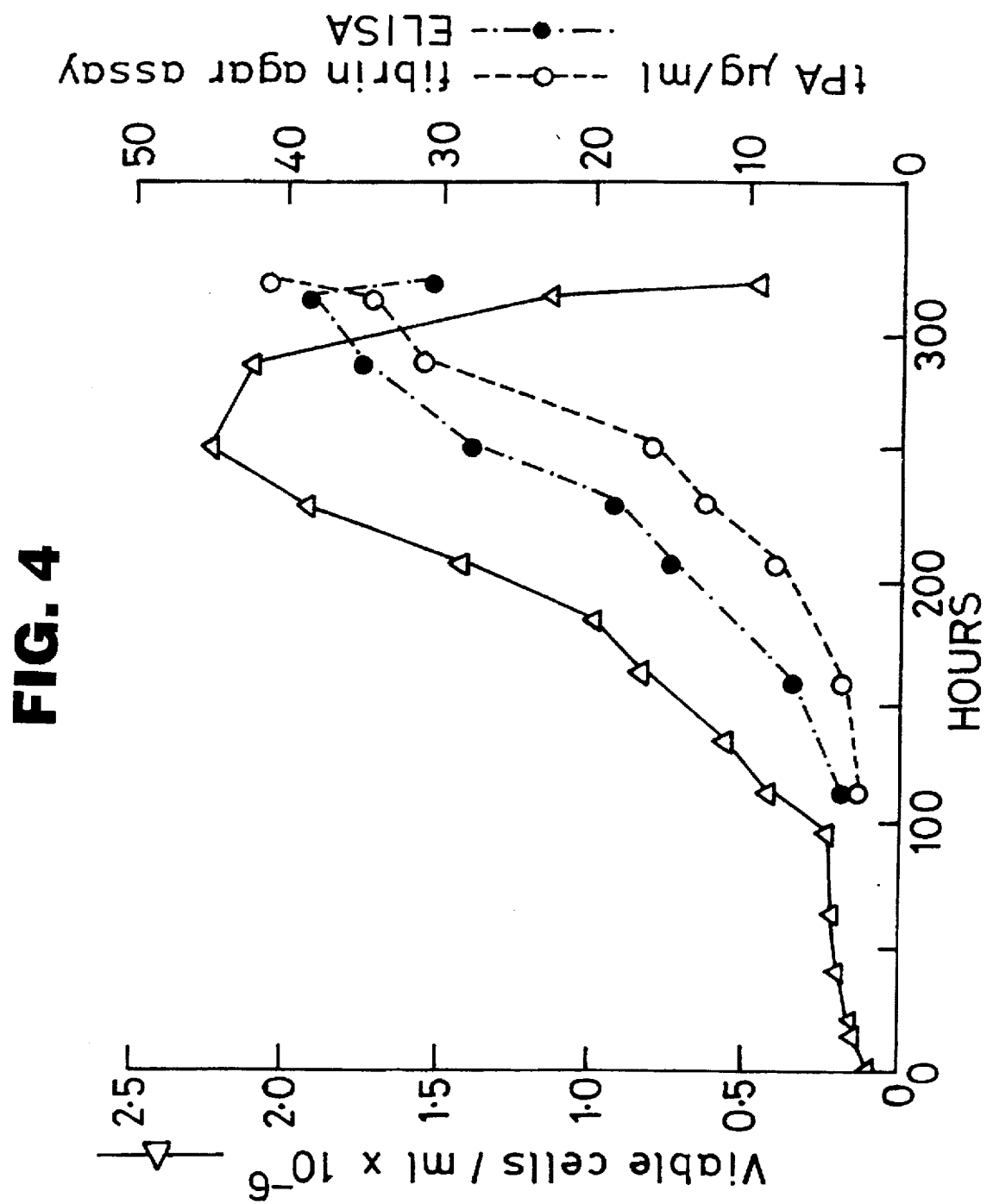

FIG. 4 is a graph showing profiles for growth and tPA synthesis by pRI 1/10 cells in an air lift fermenter (Viable cells—△—; tPA determined by ELISA—●—; tPA determined by fibrin agar assay—○—.

DESCRIPTION OF SPECIFIC EMBODIMENT

EXAMPLE 1

This example describes experiments relating to the suspension culture of hybridoma cells. The first two experiments, the batch culture and simple fed batch culture are included as comparative experiments. The experiments were carried out using a mouse-mouse hybridoma cell line, NBI which secretes a monoclonal antibody which has specificity for an antigenic determinant of B-type blood cells. The derivation and properties of NBI, alternatively known as NBI/19,112.28, are described in the specification of British Patent GB 2097425B.

1st Comparative Experiment - Batch Culture

NBI hybridoma cells were grown batchwise in an airlift fermenter in suspension in Dulbecco's Modification of Eagle's medium (DMEM) supplemented with 3% heat inactivated foetal calf serum (FCS). After an exponential growth phase lasting about 50 hours, the viable cell population density peaked at about $2 \times 10^6$ cells per ml, following which there was a sudden cessation of growth and a rapid decline in cell viability. The results of this experiment are shown in FIG. 1(a), the solid circles denoting the variation of viable cell population density and the open circles denoting the variation of antibody titre with time. The viable cells peaked at 6.4 ($\log_{10}$ viable cells/ml) and declined rapidly thereafter. The antibody titre was low and did not increase substantially following the peak of cell population density. The decline phase of the culture was shown to coincide with the depletion of glutamine from the culture medium. We therefore investigated simple fed batch cultures in which supplementary glutamine was added to the culture.

2nd Comparative Experiment - Simple Fed Batch Culture

NBI hybridoma cells were grown in suspension in FCS supplemented DMEM as in the first comparative experiment. A single shot addition of glutamine was added to the culture in the late exponential phase (to a final added concentration of 4 mM). The results obtained are shown in FIG. 1(b). The addition of glutamine did not substantially affect the maximum cell population density (solid circles) but the culture remained viable for a prolonged period with resulting increase in total antibody titre (open circles).

We also investigated the addition of repeated doses of glutamine in place of a single shot addition. The results obtained are shown in FIG. 1(c). Repeated doses (x4) of glutamine to an added concentration of 1 mM per addition over a period of 40 hours produced no improvement in cell or antibody yield compared to a single addition of 4 mM glutamine (compare FIG. 1(c) with FIG. 1(b)—the arrows in each Figure indicate the time of addition of glutamine).

We therefore analyzed culture supernatant at intervals during a glutamine fed culture, as in FIG. 1(b), and found that there was substantial depletion of other key nutrients.

Glucose, which is both an energy source and a precursor for other biomolecules, was also shown to become depleted to approximately 1% of its concentration in fresh medium. Likewise, all the component amino acids of DMEM were found to be depleted to between 10 and 50% of their starting concentrations. A means of supplying all these medium components to the culture was devised, employing shot-fed and pump-fed additions, so as to maintain each nutrient in excess for the duration of the culture. Choline, a cell membrane precursor, was also incorporated into the fed supplement.

Experiment - Fed Batch Culture

A feeding regime was tested, NBI cells were grown in a 5 liter airlift fermenter in a medium consisting of DMEM supplemented with 3% v/v foetal calf serum. The starting cell population density was approximately $0.2 \times 10^6$ viable cells/ml. When the cells had grown to a population density of approximately $1 \times 10^6$ viable cells/ml, the shot additions of supplements were made and pumped supplement initiated. The quantitative composition of the supplements was based on the patterns of nutrient utilization identified by analyses of glutamine supplemented cultures, as in FIG. 1(b). Composition of feeds and the mode of addition to the culture are summarised in Table 1. The results obtained are shown in FIG. 1(e).

TABLE 1

| COMPONENT | ADDITION mg/liter of culture | MODE OF APPLICATION |
|---|---|---|
| Supplement A | | |
| L-glutamine | 250–350 | shot-fed as 200 milli molar solution when culture is at $1 \times 10^6$ cells/ml |
| Supplement B | | |
| L-cystine | 10–40 | shot-fed as aqueous suspension when culture is at $1 \times 10^6$ cells/ml |
| L-tyrosine | 40–70 | |
| L-tryptophan | 10–20 | |
| Supplement C | | |
| L-lysine HCL | 100–140 | Pump-fed as concentrated solution in phosphated-buffered saline. Feed initiated when culture is at $1 \times 10^6$ cells/ml and continued for approx. 50 hours. |
| L-histidine | 30–40 | |
| L-arginine HCL | 60–90 | |
| L-glycine | 10–30 | |
| L-valine | 60–80 | |
| L-methionine | 20–30 | |
| L-threonine | 40–60 | |
| L-serine | 20–40 | |
| L-isoleucine | 80–100 | |
| L-leucine | 70–90 | |
| L-phenylalanine | 40–60 | |
| L-glutamine | 1000–1250 | |
| D-glucose | 4000–5000 | |
| Choline Chloride | 5–15 | |

Cells grew to a maximum viable cell population density of $2.2 \times 10^6$ cells/ml, similar to that seen in unfed and glutamine-fed cultures. However, after the growth phase there was a prolonged stationary phase during which time there was relatively little change in the viable cell population density. This was followed by a protracted decline phase (see FIG. 1(e)).

Subsequent analyses of the culture medium indicated that the major consumed nutrients were present in excess throughout the duration of the culture.

The eventual decline in cell viability was attributed to accumulation of toxic catabolites such as lactate and ammonia since these were found to be present at concentrations which we have demonstrated to be cytotoxic when added artificially to cells in early exponential growth. Also the decline of the culture was not as acute as in cultures where glutamine has become depleted.

Antibody assays were performed either by an IgM specific enzyme-linked immunosorbent assay or by a red blood cell agglutination assay. The antibody standard for the aggulation assay in this and previous experiments was culture supernatant from an unfed culture of NBI cells.

With reference to FIG. 2, antibody accumulated in the culture supernatant throughout the duration of the culture but the specific rate of antibody synthesis was found to rise from 0.3 µg/$10^6$ cells/h during the growth phase to 0.5 and to 1.5 µg/$10^6$ cells /h during the latter stages of the culture. The final antibody concentration was approximately 116 mg/liter with a red blood cell agglutination titre fourfold higher than the standard.

EXAMPLE 2

A further experiment was conducted to establish the necessity for the provision of the amino acid component of the nutrient feeds. NBI cells were grown in a 5 liter airlift fermenter in DMEM supplemented with foetal calf serum. The starting cell population density was approximately $0.2 \times 10^6$ viable cells/ml. When the cells had grown to approximately $1 \times 10^6$ viable cells/ml the culture received a shot-fed addition of glutamine to an added concentration of 2 mM and a pumped feed glutamine, glucose and choline was initiated. Thus the quantitative addition of the fed components was equivalent to the culture in Example 1 except that the culture received no supplement of insoluble or soluble amino acids apart from glutamine. The duration of the feed was approximately 50 hours. The results obtained are shown in FIG. 1(d). The growth phase of the culture followed a similar profile to that seen in the culture that received the complete feed containing amino acids. A maximum population density of $2.5 \times 10^6$ viable cells/ml was attained. However, instead of establishing a prolonged stationary phase there ensued a sudden and rapid decline in cell viability before completion of the pump-fed supplement. There was no obvious upturn in the rate of antibody synthesis during the decline of the phase of the culture. The final antibody titre was approximately half of that obtained in the culture receiving the complete feed containing supplementary amino acids.

EXAMPLE 3

Table 2 compares antibody yields obtained from conventional unfed cultures and from fed-batch cultures (feed substantially as described in the fed batch experiment of Example 1) for a number of rodent hybridoma cell lines and for a human EBV cell line. For the rodent cell lines the batch-feeding regime obtained a three to seven fold increase in antibody yields. For the human cell line batch feeding contained a 1.7 fold increase in antibody yield.

TABLE 2

Effect of nutrient feed on antibody yield from rodent hybridoma and human EBV transformed cell lines grown in batch culture.

| CELL LINE | ANTIBODY CLASS | ANTIBODY YIELD Fed-batch | Mg/l Unfed | RATIO Fed Batch:Unfed |
|---|---|---|---|---|
| 1 (Rodent) | IgG | 86 | 17 | 5.1 |
| 2 (Rodent) | IgM | 295 | 99 | 3.0 |
| 3 (Rodent) | IgG | 73 | 10 | 7.3 |
| 4 (Rodent) | IgG | 100 | 29 | 3.5 |
| 5 (Rodent) | IgG | 260 | 68 | 3.8 |
| 6 (Rodent) | IgM | 112 | 23 | 4.9 |
| 7 (Rodent) | IgG | 200 | 34 | 5.9 |
| 8 (Rodent) | IgG | 350 | 110 | 3.2 |
| 9 (Human) | IgG | 53 | 32 | 1.7 |

EXAMPLE 4

This example describes the preparation of a myeloma cell line stably transfected with a gene coding for tPA and the fed batch culturing of this cell line as in the process of the invention.

1. Vector Construction

1.1 Tissue plasminogen activator (tPA) cDNA expression constructs

The methods used in these constructions are described in detail by Maniatis et al (1982). The tPA specific DNA sequences were derived from two cDNA clones isolated from a Bowes melanoma library (Harris et al 1986). Plasmid ptPA A3 was constructed by adding HindIII linkers to a 1200 base pair bp) fragment (nucleotides 9 to 1197, Pennica et al, 1983) to tPA cDNA. The cDNA was then cloned into pAT153 at the unique HindIII site. Plasmid ptPA21 was constructed by cloning a BglII cDNA fragment (nucleotides 187 to 2166) into a plasmid with a unique BglII site. A full-length tPA cDNA gene was made by cloning the BglII fragment from ptPA21 into the BglII site of ptPA A3. The resultant plasmid ptPA 3/21 contains 76 bp of 5' non-coding sequence, the complete tPA coding region, 393 bp of 3' non-coding sequence, and a repeat segment of tPA coding region (nucleotides 187 to 1197), all on a single HindIII fragment. A second plasmid p81/11 was also constructed in which this HindIII fragment was inverted relative to pAT153 sequences.

Plasmid p81/11 was digested with BalI and the BalI fragment containing 116 nucleotides of 3' non-coding sequence, the repeated segment of tPA coding region, and some pAT153 sequences were removed leaving plasmid pBSI. Single BamHI and SalI restriction enzyme sites were re-introduced into pBSI by ligation of the 275 bp BamHI/SalI fragment from pAT 153, whose cohesive termini had been filed in with DNA polymerase, into the BalI site. Depending upon the orientation in which fragment was inserted, either a SalI site (pBS17) or a BamHI site (pBS18) was reformed at the 3' end to the tPA gene. Plasmid pBS18.was the precursor for the tPA cDNA expression constructs.

1.2 Mouse Metallothionein (MMT-I) Promoter

Clone 28 (Dr. D. Hamer; National Institute of Health, Bethesda, Md., U.S.A.) has the entire SV40 genome cloned into BamHI site and a 3.8 Kb EcoRI fragment containing the mouse metallothionein I (MMt-I) gene (Hammer and Walling, 1982) cloned into an EcoRI site. This plasmid provided the MMT-I promoter (MMT) in tPA expression constructs. The unique BglI site, 4 bp upstream of the translation start point (Glanville, et al, 1981), was converted to a HindIII site using the oligonucleotide CCAAGCTTGG.

A 2.0 Kbp HindIII fragment derived from clone 28 containing the MMT promoter was cloned into the unique HindIII site of pBS18 resulting in the formation of a transcriptional fusion between the MMT promoter and tPA coding sequences. This plasmid was called pBS18M3. A BamHI/BclI fragment of 243 bp derived from clone 28 and containing the SV40 polyadenylation site was inserted into the BamHI site of pBS18M3. The polyadenylation site was orientated in the early to late direction thus recreating a BamHI site distal to tPA gene. This plasmid was denoted p3.16 (see FIG. 3(c).

1.3 Rous Sarcoma Virus Long Terminal Repeat

The long terminal repeat (LTR) of the Rous sarcoma virus (RSV) was isolated as a ClaI/HindIII fragment from pRS-Vcat (Gorman et al 1982.) An MboII site was converted to a ClaI site using the oligonucleotide GGATCGATCC. The fragment was individually cloned into p3.16, previously cut with ClaI and HindIII, so that the MMT promoter could be replaced by the retrovirus LTR promoter. The resultant plasmid was called pRSV3 (containing the RSV LTR) (see FIG. 3(d)).

1.4 Selection Markers and other Functional Fragments

The gene responsible for conferring dominant selection was derived from pSV2 neo (Southern and Berg, 1982).

The resistance to antibiotic G418 conferred by the transcription unit in pSV2 ('neo'), was used. In order for the 'neo' transcription unit to be used it was recloned to be contained within both a BamHI and also a HindIII fragment.

The starting point for these vector constructs was pSV2 βglobin (FIG. 3(a)), (Southern and Berg, 1982). The vector's HindIII site was converted into a BglII site followed by removal of the resultant BglII fragment containing βglobin.

The resultant plasmid, pSV2 BglII formed the basis of the next step-conversion of the PvuII site into a HindIII site generating plasmid pSV3M.

The introduction of the 'neo' gene into pSV3M was via replacement of the BglII-BamHI poly A-splice gene fragment by a BglII-BamHI fragment isolated from pSV2 neo. The resultant plasmid, pSV3Mne, now contained the SV40 early promoter driving the expression of the 'neo' gene without a poly A sequence, contained within a HindIII-BamHI fragment. The HindII and BamHI sites of pSV3Mne were separately converted into BamHI and HindIII sites respectively resulting in the generation of plasmids pSV3Bne (FIG. 3(b)) and pSVMMne respectively.

In order to use pRSV3 for generation of stable cell lines, in the absence of a BPV vector conferring selection, a selection marker was introduced into the BamHI site. The selection cassette used was the BamHI fragment from pSV3Bne, producing plasmids pPRi (FIG. 3(e)) and pPRII containing the BamHI fragment in both orientations.

2. Transfection

The cell line used for transfection was YB2/3.0 Ag20 (U.K. Patent GB2070313). The cell line was maintained in Dulbecco modified Eagle's medium (DMEM, Gibco Ltd., U.K.) with penicillin (50 U/ml), streptomycin (50 ug/ml), 1 mM pyruvate, 2 mM L-glutamine and heat inactivated foetal calf serum (10%).

In order to introduce DNA into myeloma cells we have made use of the standard methods using DEAE-Dextran, $CaPO_4$ and electroporation (Banerji et al, 1983; Graham and Van der Eb, 1973; Potter et al, 1984. The majority of our transfections were made using a modification to the DEAE-Dextran method making use of dimethyl sulphoxide (DMSO) stock (Lopata et al, 1984) and chloroquinine (Lathman and Magnusson, 1983) to improve transfections.

The cells, after transfections, were typically left for 24 hours before selection was introduced. The transfections with plasmid constructs containing the 'neo' gene cassette from pSV3Bne were selected using the antibiotic G418 (Geneticin Gibco Ltd., U.K. [Schering Corp. U.S. patent specification 395254]) at a concentration of 1.4 mg/ml.

The cells, after the introduction of the selection, were allowed to incubate again for a further 24-48 hours before being plated out into microtitre dishes for clone selection. These microtitre dishes were typically incubated for 2–3 weeks before the first clones appeared. The clones were allowed to grow up to saturation (turning the culture media phenol red to yellow) prior to assaying the supernatants or to expansion into 24 well tissue culture dishes. The cell lines from those transfections which demonstrated useful levels of tPA production (greater than 100 µ/ml) were stored as frozen stocks in liquid nitrogen after supplementing the culture medium with 10% DMSO. These cell lines were also recloned and selected high producers also stored as above.

3. Quantitation of tPA protein

The tPA from cell lines was either assayed via fibrinolysis or by an enzyme linked immunosorbent assay (ELISA).

Active tPA protein in the medium was assayed using a fibrinagarose plate assay as modified by Cederholm-Williams. LGT agarose, 20 mg/ml, in 0.1 M Tris (pH7.4), 0.15 M NaCl and 2 mM $CaCl_2$ was melted and cooled to 55° C. An equal volume of fibrinogen, 2 mg/ml in 0.9% (w/v) NaCl, and human plasminogen to a final concentration of 10 ug/ml were added. Fibrin polymerisation was initiated by adding bovine thrombin to 0.12 units/ml. The mixture was poured on polyester sheets and allowed to set. Dilutions of samples and dilutions of a urokinase standard solution of known concentration (5 µl volume) were added to wells punched in the gel and the plates were incubated at 37° C. for 17 to 20 hours in a humidified chamber. The diameters of the areas of lysis were measured. A standard curve was drawn from the urokinase data by plotting the log of the diameter squared against the log of the concentration. The amount of activity in the samples was determined from the standard curve. Within the 10 to 100 units/ml range, urokinase was shown to be a suitable standard for estimating tPA activity.

Total tPA protein in culture medium from the transfected cell line was assayed using an ELISA. The ELISA was performed in Nunc Immuno assay plates (Nunc, Denmark) coated for 1 hour at 37° C. with 2 µg/ml of a goat polyclonal anti tPA (Biopool, Sewden) in 0.05 M sodium carbonate (pH9.6). These plates were blocked for one hour at 37° C. with 0.5% casein Hammerstem in 0.05 M sodium carbonate (pH9.6). These coated and blocked microtitre plates, and plates at other wash stages were washed with phosphate buffered saline, with 0.02% Tween 20. Samples for assay were diluted into sample buffer (0.1 M Tris-HCL pH7.0, 150 mN NaCl, 0.5% casein and 0.02% Tween 20). The standard used in this assay was two chain tPA (Biopool, Sweden). Samples were introduced at 100 µl per well and incubated for 1 hour at room temperature with shaking. The plates were then washed and 1 µg/ml of MACO10, a mouse monoclonal antibody to tPA, in sample buffer added to each well (100 µl). These were incubated for 1 hour at room temperature with shaking. The plates, after incubation with the monoclonal antibody, were washed and 100 µl of goat anti-mouse IgG Fc specific peroxidase conjugate was added to each well and incubated for 1 hour at room temperature with shaking. The plates, after incubation with conjugate, were washed and then developed as described (Bos et al, 1981).

4. Fibrin Agar Plate Assay

For the tPA assay, transfected cells were scraped off the plate (about $5 \times 10^6$ and 10% of the cells taken and washed twice in serum-free DMEM (Gibco), 1 mM pyruvate, 50IU/ml penicillin, 50 ug/ml streptomycin (P/S), 2 mM L-glutamine (Gln). These cells were then suspended in 7 ml of 70% DMEM as above, supplemented with 10% (v/v) acid treated foetal calf serum (FCS); 30% (v/v) Hanks balanced salts (Gibco), supplemented with 2.5% low gelling temperature agarose (Sigma Ltd.) at 42° C. This suspension was then supplemented with 0.5 units of thrombin (from bovine plasma 500U/ml, Sigma Ltd.). Finally, 1.5 mls of DMEM, 1 mM pyruvate, P/S, Gln, 10% (v/v) acid treated FCS, 30 mg/ml fibrinogen (from bovine blood, type I-S, Sigma Ltd.) was added and the mixture poured immediately into a 90 mm dish.

These dishes were incubated for times up to 48 hours in order to determine the level of tPA being produced from these transfections. The results were recorded as relative levels of fibrinolytic activity

5. tPA Producing Cell Line

The tPA producing cell line pPRI 1/10 was derived from the rat hybridoma YB2/3.0-Ag20 cell line by productively transfecting YB2/3.0-Ag20 with pPRI.

| Plasmid | YB2/3.0-Ag20 Promoter | (Maximum Levels) Maximum Units/ml of Culture |
| --- | --- | --- |
| pPRI | RSV LTR | 900 |

6. Fed Batch Culture of Cell Line pPRI 1/10 in an Airlift Fermenter

The aim of this experiment was to access growth and tPA synthesis by cell line pPRI 1/10 in a production type cell culture reactor.

The cell reactor used was an airlift fermenter (ALF) of 5 liters working volume with automatic control of dissolved oxygen tension (DOT), pH and temperature. DOT was controlled by regulated injection of air or oxygen into a sparged ballast gas of nitrogen or air. pH was controlled by regulated pump feed of alkali to the culture. Temperature was controlled by a flow of temperature regulated water to the reactor jacket.

Cell stocks of the cell line pPRI 1/10 were routinely grown in roller bottle culture in a growth medium consisting of Dulbecco's modification of Eagle's medium (DMEM) supplemented with heat-inactivated foetal calf serum (FCS) at 10% vol/vol.

Medium for the ALF culture was a serum-free formulation consisting of a DMEM base supplemented with albumin, insulin, transferrin, ethanolamine, choline, vitamins, trace metals and a shear protective polymer.

Cell inoculum for the ALF culture was grown in serum-supplemented medium. The cells were sedimented by configuration and resuspended in the serum-free growth medium prior to inoculation into the ALF. During the ALF culture supplementing nutrients were added. These consisted of:

a. a shot addition of glutamine to give an increase of 2 mM final concentration in the culture b. a shot addition of the "insoluble" amino acids tryptophan, tyrosine and cysteine c. a pumped feed consisting of glucose, choline and the "soluble" amino acids.

Samples were removed from the culture at daily intervals. Cell counts were performed using a modified Fuchs Rosenthal counting chamber and cell viability was assessed by exclusion of Trypan Blue stain. Aliquots of culture supernatant were snap frozen in liquid nitrogen and then stored at −70° C. for subsequent quantitation of tPA by tPA ELISA and fibrin agar plate assay.

FIG. 4 shows profiles for growth and tPA synthesis by pPRI 1/10 cells in airlift culture. cells attained a maximum viable population density of $2.2 \times 10^6$/ml and a maximum total population density of $4 \times 10^6$/ml. tPA was synthesised throughout the duration of the culture, reaching a maximum concentration of 42 µg/ml measured by fibrin agar plate assay and 38 µg/ml measured by the tPA ELISA. The close agreements between ELISA (which would detect both active and inactive tPA) and the fibrin agar plate assay indicates that the tPA synthesised was fully active.

The invention is described by way of illustration only in the above examples, and modifications of detail may be made within the scope of the invention.

What is claimed is:

1. A process for the fed batch culture of animal cells comprising culturing the cells in a nutrient medium through the exponential phase and into the decline phase of the culture to produce one or more cell products, wherein during the exponential growth phase of the culture and for a period of time extending beyond the exponential phase of the culture, the medium is supplemented with a combined feed comprising glutamine, at least one sugar as an energy source and one or more essential amino acids other than glutamine.

2. The process of claim 1, wherein the period of time extends into the decline phase of the culture.

3. The process of claim 1, wherein the period of time is from about 30 to about 100 hours.

4. The process of claim 1, wherein the sugar is glucose.

5. The process of claim 1, wherein the combined feed additionally comprises one or more non-essential amino acids.

6. The process of claim 1, wherein the combined feed additionally comprises choline.

7. The process of claim 1, wherein the total amount of glutamine in the combined feed is from about 0.5 to about 3 grams per liter of culture.

8. The process of claim 1, wherein the total amount of sugar in the combined feed is from about 1 to about 10 grams per liter of culture.

9. The process of claim 8, wherein the total amount of sugar in the combined feed is from about 3 to about 6 grams per liter of culture.

10. The process of claim 1, wherein the total amount of essential amino acids, excluding glutamine, in the combined feed is up to about 300 milligrams per liter of culture.

11. The process of claim 10, wherein the total amount of essential amino acids, excluding glutamine, in the combined feed is from about 20 to about 150 milligrams per liter of culture.

12. The process of claim 1, wherein the animal cells are genetically modified cells.

13. The process of claim 12, wherein the genetically modified animal cells are transfected animal cells.

14. The process of claim 12, wherein the genetically modified animal cells are antibody producing cells.

15. The process of claim 14, wherein the antibody producing cells are hybridoma cells.

16. The process of claim 13, wherein the cell product is a transfected gene product.

17. The process of claim 14, wherein the cell product is a monoclonal antibody.

18. The process of claim 16, wherein the transfected gene product is tPA.

* * * * *